United States Patent
Angel et al.

(10) Patent No.: US 11,986,527 B2
(45) Date of Patent: *May 21, 2024

(54) PHARMACEUTICAL FORMULATIONS CONTAINING CORTICOSTEROIDS FOR TOPICAL ADMINISTRATION

(71) Applicant: BAUSCH HEALTH IRELAND LIMITED, Dublin (IE)

(72) Inventors: Arturo Angel, Santa Rosa, CA (US); Gordon Dow, Greenbrae, CA (US)

(73) Assignee: BAUSCH HEALTH IRELAND LIMITED, Dublin (IE)

(*) Notice: Subject to any disclaimer, the term of this patent is extended or adjusted under 35 U.S.C. 154(b) by 0 days.

This patent is subject to a terminal disclaimer.

(21) Appl. No.: 16/174,023

(22) Filed: Oct. 29, 2018

(65) Prior Publication Data

US 2019/0083625 A1    Mar. 21, 2019

Related U.S. Application Data

(60) Division of application No. 15/966,367, filed on Apr. 30, 2018, which is a continuation-in-part of application No. 14/340,367, filed on Jul. 24, 2014, now Pat. No. 11,213,587, which is a continuation of application No. 13/287,176, filed on Nov. 2, 2011, now Pat. No. 8,809,307.

(60) Provisional application No. 61/458,339, filed on Nov. 22, 2010.

(51) Int. Cl.
| | | |
|---|---|---|
| *A61K 47/14* | (2017.01) | |
| *A61K 9/00* | (2006.01) | |
| *A61K 9/06* | (2006.01) | |
| *A61K 9/107* | (2006.01) | |
| *A61K 9/127* | (2006.01) | |
| *A61K 9/14* | (2006.01) | |
| *A61K 31/573* | (2006.01) | |
| *A61K 31/58* | (2006.01) | |
| *A61P 17/06* | (2006.01) | |

(52) U.S. Cl.
CPC ............ *A61K 47/14* (2013.01); *A61K 9/0014* (2013.01); *A61K 9/06* (2013.01); *A61K 9/107* (2013.01); *A61K 9/127* (2013.01); *A61K 31/573* (2013.01); *A61K 31/58* (2013.01); *A61P 17/06* (2018.01)

(58) Field of Classification Search
CPC ........ A61K 47/14; A61K 9/0014; A61K 9/06; A61K 9/107; A61K 9/127; A61K 31/573; A61K 31/58; A61P 17/06

See application file for complete search history.

(56) References Cited

U.S. PATENT DOCUMENTS

| | | | |
|---|---|---|---|
| 4,048,310 A | | 9/1977 | Chen et al. |
| 4,083,974 A | | 4/1978 | Turi |
| 4,233,295 A | * | 11/1980 | Hill ...................... A61K 31/585 514/174 |
| 4,244,942 A | | 1/1981 | Kamishita et al. |
| 4,299,828 A | * | 11/1981 | Wang ........................ A61J 3/08 514/174 |
| 4,370,322 A | | 1/1983 | Busse et al. |
| 4,619,921 A | | 10/1986 | Kalvoda et al. |
| 4,767,751 A | | 8/1988 | Davis |
| 4,918,065 A | | 4/1990 | Stindl et al. |
| 5,256,691 A | | 10/1993 | Suzuki |
| 5,326,566 A | | 7/1994 | Parab |
| 5,422,361 A | * | 6/1995 | Munayyer ............ A61K 9/0014 514/396 |
| 5,472,982 A | | 12/1995 | Suzuki |
| 5,972,920 A | | 10/1999 | Seidel |
| 5,990,100 A | * | 11/1999 | Rosenberg ........... A61K 9/0014 514/168 |
| 6,479,058 B1 | * | 11/2002 | McCadden ............ A61Q 17/00 424/78.05 |
| 6,517,847 B2 | | 2/2003 | Dow et al. |
| 6,579,512 B2 | | 6/2003 | Crutchfield, III |
| 6,656,928 B1 | * | 12/2003 | McCadden ............ A61K 31/56 514/167 |
| 6,765,001 B2 | | 7/2004 | Gans et al. |
| 6,974,807 B1 | | 12/2005 | Sefton |
| 7,300,669 B2 | | 11/2007 | Dow |
| 7,820,145 B2 | | 10/2010 | Tamarkin et al. |
| 8,071,578 B2 | | 12/2011 | Sefton |
| 8,808,716 B2 | | 8/2014 | Loupenok |
| 8,809,307 B2 | * | 8/2014 | Angel .................. A61K 9/0014 514/169 |
| 8,962,000 B2 | | 2/2015 | Larm |
| 8,962,028 B2 | | 2/2015 | Johnson |

(Continued)

FOREIGN PATENT DOCUMENTS

| | | |
|---|---|---|
| CA | 1303991 C | 6/1992 |
| EP | 0 513 832 A1 | 11/1992 |

(Continued)

OTHER PUBLICATIONS

Rivera et al. Topical halobetasol propionate in the treatment of plaque psoriasis. (Am. J. Clin. Dermatol., 2006; 6(5): 311-316).*

(Continued)

*Primary Examiner* — Jared Barsky

(74) *Attorney, Agent, or Firm* — Morgan, Lewis & Bockius LLP

(57) ABSTRACT

Pharmaceutical compositions for topical application to skin are provided. In some embodiments, the pharmaceutical compositions comprise a corticosteroid and further comprise a liquid oil component comprising one or more dicarboxylic acid esters and/or monocarboxylic acid esters.

18 Claims, No Drawings

(56) References Cited

U.S. PATENT DOCUMENTS

| | | |
|---|---|---|
| 9,782,341 B2 | 10/2017 | Kulesza |
| 10,478,502 B2 | 11/2019 | Angel et al. |
| 11,213,587 B2 | 1/2022 | Angel et al. |
| 2004/0081668 A1 | 4/2004 | Puglia |
| 2005/0101582 A1 | 5/2005 | Lyons |
| 2006/0018937 A1 | 1/2006 | Friedman et al. |
| 2007/0196459 A1 | 8/2007 | Zhang |
| 2008/0044444 A1 | 2/2008 | Tamarkin |
| 2009/0012051 A1 | 1/2009 | Sugishita |
| 2009/0176750 A1 | 7/2009 | Gans et al. |
| 2010/0130460 A1 | 5/2010 | Albano |
| 2010/0249060 A1 | 9/2010 | Smith |
| 2012/0129824 A1 | 5/2012 | Angel et al. |
| 2013/0310355 A1 | 11/2013 | Kulesza |
| 2014/0336161 A1 | 11/2014 | Angel |
| 2017/0266288 A1 | 9/2017 | Angel |
| 2018/0243420 A1 | 8/2018 | Angel |

FOREIGN PATENT DOCUMENTS

| | | |
|---|---|---|
| EP | 0 097 374 A2 | 1/1994 |
| EP | 0415766 B1 | 1/1997 |
| EP | 2051697 | 4/2009 |
| EP | 2494959 B1 | 11/2014 |
| GB | 1563638 | 3/1980 |
| GB | 2050831 | 9/1983 |
| GB | 2122087 | 1/1984 |
| IN | 2461/MUM/2009 | 3/2012 |
| JP | S551980-164626 | 12/1980 |
| JP | S57-093907 | 6/1982 |
| JP | S621987-215528 | 9/1987 |
| JP | S621987-238216 | 10/1987 |
| JP | S63-255227 A | 10/1988 |
| JP | S631988-255228 | 10/1988 |
| JP | H06-76328 B2 | 9/1994 |
| JP | 2004-359585 A | 12/2004 |
| JP | 2005-524614 | 8/2005 |
| NL | 7105591 A | 10/1972 |
| NZ | 208596 | 6/1984 |
| WO | 1998/36753 A1 | 8/1998 |
| WO | 1999/044585 A1 | 9/1999 |
| WO | 00/24401 A1 | 5/2000 |
| WO | 2000/040250 A1 | 7/2000 |
| WO | 2000/47211 A1 | 8/2000 |
| WO | 01/00139 A1 | 1/2001 |
| WO | 2002/11683 A1 | 2/2002 |
| WO | 2003/055445 A2 | 7/2003 |
| WO | 2007/100376 | 9/2007 |
| WO | 2008/038147 A2 | 4/2008 |
| WO | 2008/152444 | 12/2008 |
| WO | 2009/047788 | 4/2009 |
| WO | 2009/063493 | 5/2009 |
| WO | 2009/084020 A2 | 7/2009 |
| WO | 2009/158687 A1 | 12/2009 |
| WO | 2010/039251 | 4/2010 |
| WO | 2016/205001 A1 | 12/2016 |

OTHER PUBLICATIONS

Laws et al. Topical treatment of psoriasis. Expert Opin. Pharmacother. 11(12): 1999-2009, 2010.*

Smith. Podiatric Dermatology: A review of topical corticosteroids. Podiatry Management, Mar. 2006.*

Ivanova et al. in Pharm Stat. Sep. 2013; 12(5): 309-314) (Year: 2013).*

Barry, B.W., "Vasoconstrictor activities of some novel synthetic steroids in alcoholic solution," J. Investigative Dermatology, 64(6):418-422 (1975).

Davis, Adrian F. et al., "Formulation Strategies for Modulating Skin Permeation," In: Dermatological and Transdermal Formulations, Chapter 6, Edited by Kenneth A. Walters, CRC Press 2002, pp. 271-274.

Laws et al., "Topical treatment of psoriasis," Expert Opin. Pharmacother. 2010, 11(12): 1999-2009.

Remington: the Science and Practice of Pharmacy, 21st Edition, 2006, Editor David B. Troy, Lippincott Williams & Wilkins, p. 1026.

Bristol-Myers Squibb Company, Ultravate® Label, published Apr. 2003, retrieved online at <https://www.accessdata.fda.gov/drugsatfda_docs/label/2004/19967s010lbl.pdf> on May 28, 2020, 2 pages.

Budavari, S. et al. (Eds.), "4625. Halobetasol Propionate," The Merck Index: An Encyclopedia of Chemicals, Drugs, and Biologicals, Merck & Co., Inc., 12th Ed., p. 784, 1996.

Afifi, T. et al., "Topical therapies for psoriasis," Canadian Family Physician, 51:519-525, 2005.

Allergan, Inc., Label and prescribing information for Tazorac® (tazarotene) Cream, 0.05% and 0.1%, Oct. 2001, published online at <https://www.accessdata.fda.gov/drugsatfda_docs/nda/2001/21-184S001_Tazorac_prntlbl.pdf>.

Allergan, Inc., Label and prescribing information for Tazorac® (tazarotene) Cream, 0.05% and 0.1%, Dec. 2013, published online at <https://www.accessdata.fda.gov/drugsatfda_docs/label/2013/021184s007lbl.pdf>.

Baid, S. and L. Niemann, "Therapeutic doses of glucocorticoids: implications for oral medicine," Oral Diseases, 12:436-442, 2006.

Blum, G. and S. Yawalkar, "Multicenter, double-blind comparative observation of application of 0.02%, 0.05% CGP 14 458 ointments and dermovate ointment in the treatment of chronic psoriasis," Chinese Journal of Dermatology, 19(3):139-141, 1986 [with translation].

Bristol-Myers Squibb Company, Label and prescribing information for Ultravate® (halobetasol propionate ointment) Ointment, 0.05%, Apr. 2003, published online at <https://www.accessdata.fda.gov/drugsatfda_docs/label/2004/19968s007lbl.pdf>.

Carruthers, J. et al., "Observations on the systemic effect of topical clobetasol propionate (Dermovate)," British Medical Journal, 4:203-204, 1975.

Dermik Laboratories, Inc., Label and prescribing information for Psorcon® (diflorasone diacetate cream), 0.05%, Mar. 2002, revised Jan. 2009, published online at <https://dailymed.nlm.nih.gov/dailymed/fda/fdaDrugXsl.cfm?setid=a5fc8f9e-7813-45bc-a9d8-71d10f61d97b&type=display>.

E. Fougera & Co., Label and prescribing information for Betamethasone Dipropionate Gel, 0.05% (Augmented), Center for Drug Evaluation and Research, May 13, 2003, published online at <https://www.accessdata.fda.gov/drugsatfda_docs/anda/2003/75276_Betamethasone%20Dipropionate_Prntlbl.pdf>.

Fang, J. et al., "Effect of low frequency ultrasound on the in vitro percutaneous absorption of clobetasol 17-propionate," International Journal of Pharmaceutics, 191:33-42, 1999.

Feldman, S. et al., "Relative efficacy and interchangeability of various clobetasol propionate vehicles in the management of steroid-responsive dermatoses," Current Therapeutic Research, 66:154-171, 2005.

Galderma Labotatories, L.P., Label and package insert for Clobex Lotion, 0.05% (clobetasol propionate), Jul. 24, 2003, published online at <https://www.accessdata.fda.gov/drugsatfda_docs/nda/2003/21-535_Clobex_Prntlbl.pdf>.

Gao, H. and A. Li Wan Po, "Topical formulations of fluocinolone acetonide, Are creams, gels and ointments bioequivalent and does dilution affect activity?" European Journal of Clinical Pharmacology, 46:71-75, 1994.

GlaxoWellcome Inc., Label and product information for Temovate E® (clobetasol propionate emollient cream) Emollient, 0.05%, Jul. 2000, published online at <https://www.accessdata.fda.gov/drugsatfda_docs/label/2003/020340s006lbl.pdf>.

Gollnick, H. and A. Menter, "Combination therapy with tazarotene plus a topical corticosteroid for the treatment of plaque psoriasis," British Journal of Dermatology, 140(Suppl. 54): 18-23, 1999.

Harding, S. et al., "Percutaneous absorption of clobetasol propionate from novel ointment and cream formulations," Clinical and Experimental Dermatology, 10:13-21, 1985.

Hecker, D. et al., "In vitro compatibility of tazarotene with other topical treatments of psoriasis," J. Am. Acad. Dermatol., 42:1008-1011, 2000.

(56) References Cited

OTHER PUBLICATIONS

Hu, Z. et al., "Efficacy of 0.05% CGP 14 458 ointment in the treatment of psoriasis and its effects on adrenal function," Chinese Journal of Dermatology, 21(5):291-292, 1988 [with translation].
Ismail, I. et al., "Subchronic and chronic toxicity of tazarotene gel following topical application in Hanford miniswine," International Journal of Toxicology, 16:571-584, 1997.
Kaidbey, K. et al., "A pilot study to determine the effect of tazarotene gel 0.1% on steroid-induced epidermal atrophy," International Journal of Dermatology, 40:468-471, 2001.
Kalvoda, J. et al. "Concept and development of a potent topical corticosteroid," Chimia International Journal for Chemistry, 46(7-8):338-344, 1992.
Koo, J. et al., "Investigator-masked comparison of tazarotene gel q.d. plus mometasone furoate cream q.d. vs. mometasone furoate cream b.i.d. in the treatment of plaque psoriasis," International Journal of Dermatology, 40:210-215, 2001.
Krueger, G. et al., "The Safety and efficacy of tazarotene gel, a topical acetylenic retinoid, in the treatment of psoriasis," Arch. Dermatol., 134:57-60, 1998.
Lebwohl, M. et al., "Topical application of calcipotriene and corticosteroids: Combination regimens," J. Am. Acad. Dermatol., 37:S55-S58, 1997.
Lebwohl, M. et al., Tazarotene 0.1% gel plus corticosteroid cream in the treatment of plaque psoriasis, J. Am. Acad. Dermatol., 39:590-6, 1998.
Lebwohl, M. et al., "Tazarotene in combination with topical corticosteroids," J. Am. Acad. Dermatol., 39:S139-43, 1998.
Loder, J. et al., "Halobetasol Propionate," in *Topical Corticosteroids*, S. Karger AG, Switzerland, 1992, pp. 423-434.
Lubrizol Advanced Materials, Inc., Product Guide and Regulatory Overview for Carbomer Homopolymer, Jun. 2011.
Lubrizol Advanced Materials, Inc., "Introducing Pemulen® Polymeric Emulsifiers," Technical Data Sheet (TDS-114), Oct. 15, 2007, published online at <https://www.lubrizol.com/-/media/Lubrizol/Life-Sciences/Documents/TDS/TDS-114_Introducing_Pemulen_Polymeric_Emulsifiers.pdf>.
Lubrizol Advanced Materials, Inc., "Emulsification Properties," Pharmaceutical Bulletin 8, Oct. 29, 2008, published online at <https://www.lubrizol.com/-/media/Lubrizol/Health/Literature/Bulletin-08---Emulsification-Properties.pdf>.
Medicis, Label and prescribing information for Vanos™ (fluocinonide) Cream, 0.1%, Mar. 2006, published online at <https://www.accessdata.fda.gov/drugsatfda_docs/label/2006/021758s00lbl.pdf>.
O'Neil, M. et al. (Eds.), *The Merck Index: An Encyclopedia of Chemicals, Drugs, and Biologicals*, Merck & Co., Inc., USA, 13th ed., 1996, pp. 200-201, 413, 552, and 735.
Okuyama, H. et al., "Influence of additives on percutaneous absorption of piroxicam from cataplasm," Drug Delivery System, 14(6):491-497, 1999 [with English translation].
Ostrenga, J. et al., "Vehicle design for a new topical steroid, fluocinonide," The Journal of Investigative Dermatology, 56(5):392-399, 1971.
Ozawa, Y. et al., "Influence of fatty acid-alcohol esters on percutaneous absorption of hydrocortisone butyrate propionate," Chem. Pharm. Bull., 36(6):2145-2151, 1988.
Ranbaxy, Label and prescribing information for Ultravate® (halobetasol propionate) Cream, 0.05% and (halobetasol propionate) Ointment, 0.05%, Mar. 2012, published online at <https://www.accessdata.fda.gov/drugsatfda_docs/label/2012/019968s011lbl.pdf>.
Rowe, R. et al. (Eds.), *Handbook of Pharmaceutical Excipients*, Pharmaceutical Press and American Pharmacists Association, 6th ed., 2009, pp. 110-114, 445-449, and 675-678.
Ryatt, K. et al., "The stability and blanching efficacy of betamethasone-17-valerate in emulsifying ointment," British Journal of Dermatology 107:71-76, 1982.
Schering-Plough Pty Limited, Label and Product Information for Diprosone® OV Cream and Ointment (Betamethasone dipropionate), Aug. 26, 2008, published online at <https://www.tga.gov.au/sites/default/files/foi-065-1718-03.pdf>.
Shah, V. et al., "Bioequivalence of Topical Dermatological Products," in *Topical Drug Bioavailability, Bioequivalence, and Penetration*, Plenum Press, USA, 1993, pp. 393-413.
Surber, C. and A. Davis, "Bioavailability and Bioequivalence of Dermatological Formulations," in *Dermatological and Transdermal Formulations*, Marcel Dekker, Inc., USA, 2002, pp. 401-498.
Taropharma, Product Monograph for Lyderm Ointment (Fluocinonide Ointment USP, 0.05%), Lyderm Gel (Fluocinonide Gel USP, 0.05%), and Lyderm Cream (Fluocinonide Cream USP, 0.05%), Sep. 2, 2003, published online at <https://pdf.hres.ca/dpd_pm/00004233.PDF>.
Thomson PDR, "Ultravate®," in *Physicians' Desk Reference*, Thomson PDR, USA, 58th ed., 2004, pp. 1100-1102.
U.S. National Library of Medicine (ClinicalTrials.gov), Study Record Detail: Tabular View, Study No. NCT02045277: Safety and Efficacy of IDP-118 in the Treatment of Plaque Psoriasis, Aug. 20, 2020, published online at <https://clinicaltrials.gov/ct2/show/record/NCT02045277?term=NCT02045277&draw=2&rank=1>.
U.S. National Library of Medicine (ClinicalTrials.gov), Study Record Detail: Study Results, Study No. NCT02045277: Safety and Efficacy of IDP-118 in the Treatment of Plaque Psoriasis, Aug. 20, 2020, published online at <https://clinicaltrials.gov/ct2/show/results/NCT02045277?term=NCT02045277&draw=2&rank=1>.
U.S. National Library of Medicine (ClinicalTrials.gov), History of Changes for Study No. NCT02045277: Safety and Efficacy of IDP-118 in the Treatment of Plaque Psoriasis, Study Record Version 1, Jan. 22, 2014, published online at <https://clinicaltrials.gov/ct2/history/NCT02045277?V_1=View#StudyPageTop>.
U.S. National Library of Medicine (ClinicalTrials.gov), History of Changes for Study No. NCT02045277: Safety and Efficacy of IDP-118 in the Treatment of Plaque Psoriasis, Study Record Version 2, Feb. 19, 2014, published online at <https://clinicaltrials.gov/ct2/history/NCT02045277?V_2=View#StudyPageTop>.
U.S. National Library of Medicine (ClinicalTrials.gov), History of Changes for Study No. NCT02045277: Safety and Efficacy of IDP-118 in the Treatment of Plaque Psoriasis, Study Record Version 3, Apr. 30, 2014, published online at <https://clinicaltrials.gov/ct2/history/NCT02045277?V_3=View#StudyPageTop>.
U.S. National Library of Medicine (ClinicalTrials.gov), History of Changes for Study No. NCT02045277: Safety and Efficacy of IDP-118 in the Treatment of Plaque Psoriasis, Study Record Version 4, Dec. 8, 2014, published online at <https://clinicaltrials.gov/ct2/history/NCT02045277?V_4=View#StudyPageTop>.
U.S. National Library of Medicine (ClinicalTrials.gov), History of Changes for Study No. NCT02045277: Safety and Efficacy of IDP-118 in the Treatment of Plaque Psoriasis, Study Record Version 5, Aug. 15, 2016, published online at <https://clinicaltrials.gov/ct2/history/NCT02045277?V_5=View#StudyPageTop>.
U.S. National Library of Medicine (ClinicalTrials.gov), History of Changes for Study No. NCT02045277: Safety and Efficacy of IDP-118 in the Treatment of Plaque Psoriasis, Comparison of Study Record Version 4, Dec. 8, 2014, and Version 5, Aug. 15, 2016, published online at <https://clinicaltrials.gov/ct2/history/NCT02045277?A=4&B=5&C-Side-by-Side#StudyPageTop>.
U.S. National Library of Medicine (ClinicalTrials.gov), History of Changes for Study No. NCT02045277: Safety and Efficacy of IDP-118 in the Treatment of Plaque Psoriasis, Study Record Version 6, Dec. 13, 2017, published online at <https://clinicaltrials.gov/ct2/history/NCT02045277?V_6=View#StudyPageTop>.
U.S. National Library of Medicine (ClinicalTrials.gov), History of Changes for Study No. NCT02045277: Safety and Efficacy of IDP-118 in the Treatment of Plaque Psoriasis, Study Record Version 7, Aug. 8, 2020, published online at <https://clinicaltrials.gov/ct2/history/NCT02045277?V_7=View#StudyPageTop>.
U.S. National Library of Medicine (ClinicalTrials.gov), Study Record Detail: Study Details, Study No. NCT01670513: A Phase 2 Dosing Ranging, Evaluator-Blinded Study to Evaluate the Safety of Topical IDP-118, Apr. 25, 2013, published online at <https://clinicaltrials.gov/ct2/show/study/NCT01670513>.
U.S. National Library of Medicine (ClinicalTrials.gov), Study Record Detail: No Results Posted, Study No. NCT01670513: A Phase 2 Dosing Ranging, Evaluator-Blinded Study to Evaluate the Safety of

(56) References Cited

OTHER PUBLICATIONS

Topical IDP-118, Apr. 25, 2013, published online at <https://clinicaltrials.gov/ct2/show/results/NCT01670513>.
U.S. National Library of Medicine (ClinicalTrials.gov), Study Record Detail: Tabular View, Study No. NCT01670513: A Phase 2 Dosing Ranging, Evaluator-Blinded Study to Evaluate the Safety of Topical IDP-118, Apr. 25, 2013, published online at <https://clinicaltrials.gov/ct2/show/record/NCT01670513>.
U.S. National Library of Medicine (ClinicalTrials.gov), History of Changes for Study No. NCT01670513: A Phase 2 Dosing Ranging, Evaluator-Blinded Study to Evaluate the Safety of Topical IDP-118, Study Record Version 1, Aug. 20, 2012, published online at <https://clinicaltrials.gov/ct2/history/NCT01670513?V_1=View#StudyPageTop>.
U.S. National Library of Medicine (ClinicalTrials.gov), History of Changes for Study No. NCT01670513: A Phase 2 Dosing Ranging, Evaluator-Blinded Study to Evaluate the Safety of Topical IDP-118, Study Record Version 2, Apr. 23, 2013, published online at <https://clinicaltrials.gov/ct2/history/NCT01670513?V_2=View#StudyPageTop>.
Weinberg, J. (ed.), *Treatment of Psoriasis*, Birkhäuser Verlag AG, Switzerland, 2008, pp. 1-70.
Westwood-Squibb Pharmaceuticals Inc., Patient information leaflet for Ultravate® (halobetasol propionate cream) Cream, 0.05%, 1995, published online at <https://www.accessdata.fda.gov/drugsatfda_docs/label/2003/019967s004lbl.pdf>.
Zografi, G. et al., "Interfacial Phenomena," in *Remington's Pharmaceutical Sciences*, Mack Publishing Co., USA, 18th ed., 1990, pp. 257-309.
Fiume et al., Int J Toxicol. Jul.-Aug. 2012;31(4 Suppl):5S-76S.
Gennaro A., Remington's Pharmaceutical Sciences (18th ed. 1990), p. 271 and 305.
Eastman, William J. et al., "Assessing Attributes of Topical Vehicles for the Treatment of Acne, Atopic Dermatitis, and Plaque Psoriasis," Cutis, 2014, vol. 94, pp. 46-53.
Ghosh Mridul K. and Ashim K. Mitra. Carboxylic Ester Hydrolase Activity in Hairless and Athymic Nude Mouse Skin. Pharmaceutical Research, vol. 7, No. 3 (1990) 251-255.
Guenther, Lyn C., "Optimizing Treatment with Topical Tazarotene," American Journal of Clinical Dermatology, 2003, vol. 4, No. 3, pp. 197-202.
Kasongo, Kasongo Wa. Development and In Vitro Evaluation of a Clobetasol 17-Propionate Topical Cream Formulation. Master of Science Thesis, Rhodes University, Jan. 2007, 252 pages.
Leyden, James J., "Meta-Analysis of Topical Tazarotene in the Treatment of Mild to Moderate Acne," Cutis, Oct. 2004, vol. 74(suppl 4), pp. 9-15.
Michniak, Bozena B. et al. Facilitated Transport of Two Model Steroids by Esters and Amides of Clofibric Acid. Journal of Pharmaceutical Sciences, vol. 82, No. 2, Feb. 1993, 214-219.
Poulin, Yves P., "Tazarotene 0.1% Gel in Combination with Mometasone Furoate Cream in Plaque Psoriasis: A Photographic Tracking Study," Cutis, Jan. 1999, vol. 63, No. 1, pp. 41-48.
Puig, L. et al., "Adherence and Patient Satisfaction With Topical Treatment in Psoriasis, and the Use, and Organoleptic Properties of Such Treatments: A Delphi Study With an Expert Panel and Members of the Psoriasis Group of the Spanish Academy of Dermatology and Venereology," Actas Dermo Sifiliograficas, 2013, vol. 104, No. 6, pp. 488-496.
Refai, H. Dilution of Semisolid Preparations. Thesis, Institute at Pharmazeutische Technologie, Technische Universitat Carolo-Wilhelmina, Braunschweig., Mar. 2001, 152 pages.
Sintov A. Cumulative evidence of the low reliability of frozen/thawed pig skin as a model for in vitro percutaneous permeation testing, European Journal of Pharmaceutical Sciences 102 (2017) 261-263.
Tanghetti, Emil et al., "Randomized Comparison of the Safety and Efficacy of Tazarotene 0.1% Cream and Adapalene 0.3% Gel in the Treatment of Patients With at Least Moderate Facial Acne Vulgaris," Journal of Drugs in Dermatology, May 2010, vol. 9, issue 5, pp. 549-558.
U.S. District Court, District of New Jersey, Opinion, *Bausch Health Ireland Limited* v. *Padagis Israel Pharmaceuticals Ltd*, Case 2:20-cv-05426-SRC-CLW Document 246 Filed Dec. 1, 2022, 77 pages.
European Search Report for related European Patent Application No. 22215648.1 dated Oct. 6, 2023, 14 pages.
Korting H C et al: "Topical glucocorticoids with improved benefit/risk ratio: Do they exist?", Journal of the American Academy of Dermatology, Mosby, Inc, US, vol. 27, No. 1, Jul. 1, 1992 (Jul. 1, 1992), pp. 87-92, XP025613515, ISSN: 0190-9622, DOI: 10.1016/0190-9622(92)70162-9.

\* cited by examiner

PHARMACEUTICAL FORMULATIONS CONTAINING CORTICOSTEROIDS FOR TOPICAL ADMINISTRATION

CROSS-REFERENCE TO RELATED APPLICATIONS

This application is a divisional of U.S. patent application Ser. No. 15/966,367, filed Apr. 30, 2018, which is a continuation-in-part of U.S. patent application Ser. No. 14/340,367, filed Jul. 24, 2014, which is a continuation of U.S. patent application Ser. No. 13/287,176, filed Nov. 2, 2011, issued as U.S. Pat. No. 8,809,307, which claims priority to U.S. Provisional Patent Application Ser. No. 61/458,339, filed on Nov. 22, 2010.

BACKGROUND OF THE INVENTION

Topical corticosteroids are used to treat many acute and chronic dermatologic and mucosal disorders, especially those in which pruritus or inflammation is present. Many such conditions, such as eczema, psoriasis, and chronic dermatitis, such as hand dermatitis, are chronic conditions that require long-term therapy.

Corticosteroids for topical application are grouped within a classification system into seven classes based on potency. Topical potency of a corticosteroid is determined by a standard test, referred to as a VasoConstrictor Assay (VCA). The VCA test is described in Dow et al., U.S. Pat. No. 7,300,669, incorporated herein by reference.

Table 1 below shows the classification of topical corticosteroids based on potency as determined by the VCA test. See, Ference et al., *Am Fam Physician*, 2009, 79:135-140.

TABLE 1

Potency Chart of Topical Corticosteroids
Potency Chart of Topical Corticosteroids Class 1 - Superpotent Clobetasol propionate 0.05%
Augmented betamethasone dipropionate gel/ointment 0.05% (Diprolene ®)
Halobetasol propionate 0.05%
Fluocinonide 0.1%
Diflorasone diacetate ointment 0.05% (Psorcon ®)
Class 2 - Potent Augmented betamethasone dipropionate cream/lotion 0.05% (Diprolene ®)
Betamethasone dipropionate ointment 0.05% (Diprosone ®)
Mometasone furoate ointment 0.1%
Diflorasone diacetate cream 0.05% (Psorcon ®)
Diflorasone diacetate ointment 0.05% (Florone ®)
Halcinonide 0.1%
Desoximetasone cream/ointment 0.25%
Desoximetasone gel 0.05%
Fluocinonide cream/gel/ointment 0.05% (Lidex ®)
Amcinonide 0.1%
Budesonide 0.025%
Beclomethasone 0.025%
Class 3 - Upper Mid-strength Fluticasone propionate ointment 0.005%
Fluocinonide cream 0.05% (Lidex-E ®)
Betamethasone dipropionate cream 0.05% (Betanate ®)
Betamethasone valerate 0.12%
Class 4 - Mid-strength Flurandrenolide ointment 0.05%
Mometasone furoate cream 0.1%
Triamcinolone acetonide 0.1%

TABLE 1-continued

Potency Chart of Topical Corticosteroids
Potency Chart of Topical Corticosteroids Fluocinolone acetonide 0.03%
Hydrocortisone valerate 0.2%
Desoximetasone cream/ointment 0.05% (Topicort ® LP)
Class 5 - Lower Mid-strength Fluocinolone acetonide shampoo 0.01%
Flurandrenolide cream/lotion/tape 0.05%
Fluticasone propionate cream/lotion 0.05%
Prednicarbate cream 0.1%
Desonide lotion 0.05%
Hydrocortisone butyrate cream/lotion/ointment/solution 0.1% (Locoid ®)
Hydrocortisone probutate cream 0.1% (Pander ®)
Fluocinolone acetonide cream 0.03%/0.01% (Synalar ®)
Hydrocortisone valerate cream 0.2%
Class 6 - Mild Alclometasone dipropionate 0.05%
Fluocinolone acetonide oil 0.01%
Desonide gel 0.05%
Fluocinonide cream/solution 0.01%
Desonide foam 0.05%
Class 7 - Least Potent Hydrocortisone lotion 0.5%/1%
Hydrocortisone cream/spray/ointment 1%
Hydrocortisone cream/lotion 1%/2.5%

The most potent group of corticosteroids, determined on the basis of the VCA, is denoted Class 1 superpotent corticosteroids. In this specification, when a concentration is indicated with a particular corticosteroid, for example as an ester, an acetonide, a free alcohol, or a diester, the corticosteroid is stated as a particular form of the corticosteroid. When no concentration is indicated with a corticosteroid, or when a concentration refers to the corticosteroid in more than one form, such as an ester, an acetonide, a free alcohol, or a diester, the corticosteroid is stated without reference to the particular form. All known preparations of clobetasol propionate and halobetasol propionate, all of which are at a concentration of 0.05% w/w, are classed as superpotent corticosteroids. Other corticosteroids classified as superpotent are certain preparations of betamethasone dipropionate at a concentration of 0.05%, diflorasone diacetate at a concentration of 0.05%, and fluocinonide at a concentration of 0.1%. The next most potent group of corticosteroids is denoted Class 2 potent corticosteroids. This group includes mometasone furoate at a concentration of 0.1%, halcinonide, diflorasone diacetate, desoximetasone, fluocinonide at a concentration of 0.05%, and cream formulations of betamethasone at a concentration of 0.05%.

The superpotent corticosteroids are utilized for skin conditions that are not satisfactorily responsive to lower potency corticosteroids. Such conditions include psoriasis and certain severe types of eczema. Unfortunately, because of the high potency of the Class 1 corticosteroids, which correlates with a high incidence and severity of systemic side effects, including hypothalamic-pituitary-adrenal (HPA) axis suppression, topical treatment with superpotent corticosteroids is generally limited in duration to 2 weeks. Such side effects may also occur with treatment with Class 2 potent corticosteroids. Additionally, the occurrence of local adverse reactions limits the duration of use of superpotent and potent corticosteroids with respect to treatment of chronic or recurrent skin diseases.

Chronic skin conditions, such as psoriasis, however often require long periods of treatment, greater than 2 weeks, to manage such conditions. Therefore, it would be desirable to have a superpotent corticosteroid formulation with a reduced incidence and/or severity of systemic side effects so that therapy can be continued for durations longer than 2 weeks.

Dow, U.S. Patent Publication 2006/0239929, discloses a spray formulation containing 0.05% clobetasol that was shown to be efficacious and to have few serious side effects when administered for periods of 4 weeks. The disclosure of Dow, however, was limited to a spray formulation and the prosecution history of this application shows that prior art formulations of 0.05% clobetasol are associated with high frequencies of serious systemic side effects, including hypothalamic-pituitary-adrenal axis suppression when applied for a period of 2 weeks.

Because of the tendency of all superpotent corticosteroids to cause serious systemic effects, the FDA (Food and Drug Administration) requires that the prescribing information for currently marketed topical compositions of superpotent corticosteroids, such as clobetasol and halobetasol, except for a particular spray formulation of clobetasol, carry the warning that treatment beyond 2 consecutive weeks is not recommended, and the total dosage should not exceed 50 g of the composition per week. Regarding the clobetasol spray formulation, the prescribing information states that treatment should be limited to 4 weeks and that treatment beyond 2 weeks should be limited to localized lesions of moderate to severe plaque psoriasis that have not sufficiently improved after two weeks. Regarding potent corticosteroids, the FDA does not require the prescribing information to carry this warning, but does caution the physician to be aware of and to monitor for the occurrence of HPA axis suppression.

Busse, U.S. Pat. No. 4,370,322, concerns the problem of systemic side effects due to topical application of high-potency corticosteroids. Busse discloses a topical pharmaceutical composition containing a high-potency corticosteroid and an oil phase that contains a low viscosity oily solvent, wherein the concentration of the liquid oil phase is at least three times that which is required to completely solubilize the corticosteroid. Busse discloses that, when the solvent-containing oil phase is present in such high concentrations relative to the corticosteroid, the systemic absorption of the corticosteroid is reduced but the local, desirable effects of the corticosteroid are maintained. Busse further disclose that this discovery permits the application of the same amount of steroid to achieve the same local anti-inflammatory effect while reducing unwanted systemic effects.

Parab, U.S. Pat. No. 5,326,566, in contrast to the disclosure of Busse which discloses that a high concentration oily phase will decrease systemic absorption of a corticosteroid when applied to the skin, discloses that, when a formulation contains a skin penetration enhancing amount of dibutyl adipate or a mixture of dibutyl adipate and isopropyl myristate at a concentration that is sufficient to dissolve the corticosteroid in the formulation but which is less than 1.5 times that which is required to dissolve the corticosteroid, the penetration of the corticosteroid through skin and into the systemic circulation is increased rather than decreased. Thus, Parab discloses that formulations containing a corticosteroid and an oily phase containing dibutyl adipate, alone or in combination with isopropyl myristate, at a concentration between 1 and 1.5 times that required to dissolve the corticosteroid are useful for increasing the systemic absorption of a topically applied corticosteroid.

SUMMARY OF THE INVENTION

In one aspect, pharmaceutical compositions for topical application to the skin of an individual are provided. In some embodiments, the composition comprises:

a liquid oil component comprising one or more monocarboxylic acid esters and/or dicarboxylic acid esters, wherein the liquid oil component further comprises a corticosteroid at a concentration less than 0.05% (w/w), and wherein at least 25% of the corticosteroid is solubilized in the liquid oil component at a temperature of 22° C.±2° C.; and an aqueous component comprising water.

In some embodiments, the corticosteroid is a superpotent (i.e., Class I) corticosteroid, a potent (i.e., Class II) corticosteroid, or a mid-potent (i.e., Class III) corticosteroid (e.g., as disclosed in Table 1 above). In some embodiments, the corticosteroid is selected from the group consisting of clobetasol propionate, betamethasone dipropionate, halobetasol propionate, diflorasone diacetate, desoximetasone, mometasone furoate, betamethasone valerate, halcinonide, fluocinonide, or amcinonide.

In some embodiments, the liquid oil component comprises a corticosteroid selected from the group consisting of clobetasol propionate, betamethasone dipropionate, diflorasone diacetate, and desoximetasone at a concentration less than 0.05% (w/w). In some embodiments, the corticosteroid is clobetasol. In some embodiments, the corticosteroid is clobetasol propionate. In some embodiments, the corticosteroid is betamethasone. In some embodiments, the corticosteroid is betamethasone dipropionate. In some embodiments, the corticosteroid is diflorasone. In some embodiments, the corticosteroid is diflorasone diacetate. In some embodiments, the corticosteroid is desoximetasone.

In some embodiments, the concentration of the corticosteroid (e.g., a superpotent corticosteroid, a potent corticosteroid, or a mid-potent corticosteroid) is about 0.045% or less. In some embodiments, the concentration of the corticosteroid is about 0.04% or less. In some embodiments, the concentration of the corticosteroid is about 0.03% or less. In some embodiments, the concentration of the corticosteroid is about 0.02% or less. In some embodiments, the concentration of the corticosteroid is about 0.01% or less. In some embodiments, the concentration of the corticosteroid is about 0.045%. In some embodiments, the concentration of the corticosteroid is about 0.04%. In some embodiments, the concentration of the corticosteroid is about 0.035%. In some embodiments, the concentration of the corticosteroid is about 0.03%. In some embodiments, the concentration of the corticosteroid is about 0.025%. In some embodiments, the concentration of the corticosteroid is about 0.02%. In some embodiments, the concentration of the corticosteroid is about 0.015%. In some embodiments, the concentration of the corticosteroid is about 0.01%.

In some embodiments, the liquid oil component comprises a dicarboxylic acid ester. In some embodiments, the dicarboxylic acid ester is diethyl sebacate. In some embodiments, the liquid oil component comprises a monocarboxylic acid ester. In some embodiments, the monocarboxylic acid ester is isopropyl myristate. In some embodiments, the liquid oil component further comprises mineral oil or light mineral oil.

In some embodiments, the concentration of the liquid oil component is sufficient to dissolve the amount of corticosteroid in the composition at a temperature of 22° C.±2° C. In some embodiments, the concentration of the liquid oil component is between 1.5 and 3 times that required to completely solubilize the amount of corticosteroid in the composition at a temperature of 22° C.±2° C. In some embodiments, the concentration of the liquid oil component is between 1.75 and 2.75 times that required to completely solubilize the amount of corticosteroid in the composition at a temperature of 22° C.±2° C.

In some embodiments, the liquid oil component further comprises an emulsifying agent. In some embodiments, the emulsifying agent is sorbitan monooleate.

In some embodiments, the aqueous component further comprises one or more humectants, preservatives, chelating agents, emulsifying agents, and/or thickening agents. In some embodiments, the aqueous component comprises a humectant and the humectant is sorbitol or propylene glycol. In some embodiments, the aqueous component comprises a preservative and the preservative is benzyl alcohol, methylparaben, and/or propylparaben. In some embodiments, the aqueous component comprises a chelating agent and the chelating agent is edetate disodium dihydrate. In some embodiments, the aqueous component comprises an emulsifying agent and the emulsifying agent is a polymeric emulsifier. In some embodiments, the aqueous component comprises a thickening agent and the thickening agent is a carboxyvinyl polymer.

In some embodiments, the composition further comprises a pH adjusting agent. In some embodiments, the pH adjusting agent is sodium hydroxide.

In some embodiments, the composition is formulated as an oil-in-water emulsion, a water-in-oil emulsion, an oil-in-water-in-oil emulsion, or a microglobular emulsion. In some embodiments, the composition is formulated as a lotion or a cream.

In another aspect, methods of treating a dermatological or mucosal disorder or condition are provided. In some embodiments, the method comprises topically administering a corticosteroid composition formulated as disclosed herein to the skin of an individual having the dermatological or mucosal disorder or condition. In some embodiments, the dermatological or mucosal disorder or condition is psoriasis, plaque psoriasis, atopic dermatitis, contact dermatitis, hand dermatitis, eczema, seborrheic dermatitis, rash, lichen planus, lichen sclerosus, or poison ivy dermatitis. In some embodiments, the dermatological or mucosal disorder or condition is psoriasis. In some embodiments, the dermatological or mucosal disorder or condition is plaque psoriasis. In some embodiments, the method comprises administering the corticosteroid composition for a period of treatment equal to or longer than two weeks (e.g., longer than three weeks, longer than four weeks, or longer than 1, 2, 3, 4, 5, or 6 months). In some embodiments, the method comprises administering the corticosteroid composition for a period of treatment up to two weeks. In some embodiments, the method comprises administering the corticosteroid composition until complete clearance of the afflicted skin is achieved. In some embodiments, the method comprises administering the corticosteroid composition once, twice, or three times a day to an area of afflicted skin.

DETAILED DESCRIPTION OF THE INVENTION

It has been unexpectedly discovered that the potency of a topical corticosteroid, including superpotent, potent, and mid-potent topical corticosteroids as determined by the VCA test described above, is maintained even when the concentration of the corticosteroid is substantially reduced by providing the corticosteroid in a formulation containing a liquid oil component that includes a dicarboxylic acid ester and/or a monocarboxylic acid ester. Because the potency of the corticosteroid is maintained, even when the concentration of the corticosteroid is markedly reduced, the desired dermatological effects of the treatment are obtained. Due to the much reduced concentration of the corticosteroid in the formulation, reduced amounts of corticosteroid are available to enter the systemic circulation and, therefore, the tendency of such formulations to cause undesirable systemic side effects should likewise be reduced. Thus, the formulations and methods of this application are especially useful for the treatment of chronic or recalcitrant skin diseases, such as psoriasis, plaque psoriasis, atopic dermatitis, contact dermatitis, hand dermatitis, eczema, seborrheic dermatitis, rash, or poison ivy dermatitis, due to the concerns regarding safety when topical corticosteroids are used in multiple course treatments over time.

Accordingly, one embodiment of the invention is a pharmaceutical formulation for topical administration to the skin which contains a corticosteroid at a concentration below that which is presently utilized in topical formulations (e.g., as disclosed in Table 1 above) and which provides substantially an equivalent potency to formulations having the higher concentrations that are presently utilized. Thus, for superpotent corticosteroids other than fluocinonide, such as halobetasol propionate and clobetasol propionate, the formulation contains the corticosteroid at a concentration less than 0.05% (w/w) and for fluocinonide, the formulation contains the corticosteroid at a concentration less than 0.1% (w/w). Similarly, for potent and mid-potent corticosteroids other than mometasone, halcinonide, and beclomethasone, the formulation may contain the corticosteroid at a concentration less than 0.05%, and in the case of mometasone or halcinonide, less than 0.1%, and in the case of beclomethasone, less than 0.025%.

The liquid oil component of the present application includes all ingredients of the formulation that are practically insoluble or insoluble in water and which are liquid at room temperature of 22° C. Other than the dicarboxylic acid ester and monocarboxylic acid esters discussed herein, the liquid oil component may contain additional components such as hydrocarbons like mineral oil, light mineral oil, squalene, and squalane, fatty alcohols such as octylododecanol, castor oil, oleyl alcohol, and isostearyl alcohol, fatty acids such as isostearic acid and oleic acid, and triglycerides such as peanut oil, and fractionated coconut oil.

In addition to the liquid oil component, the formulation may contain water insoluble or practically insoluble ingredients that are not liquid at room temperature. However, as discussed in further detail below, it is the liquid oil component of the formulation that is of importance in relation to the reduced concentration of the corticosteroid in the formulation.

The liquid oil component containing the dicarboxylic acid ester and/or the monocarboxylic acid ester in the formulation is in association with the corticosteroid in the formulation, such that the liquid oil component and the corticosteroid may interact in the formulation in order to dissolve or substantially dissolve the corticosteroid. It is hypothesized that it is this solubilization within the formulation, coupled with its polymeric emulsification system that, upon application of the formulation to the skin of a patient, provides delivery of the corticosteroid preferentially into the skin. As used herein, the term "substantially dissolve" means that the liquid oil component of a formulation of this invention can dissolve 25% or more of the corticosteroid in the formulation at a room temperature of 22° C.

Corticosteroid

In some embodiments, the formulation comprises a corticosteroid disclosed in Table 1 above. In some embodiments, the corticosteroid that is included in the formulation of the invention is preferably a superpotent corticosteroid according to the VasoConstrictor Assay (VCA), such as clobetasol, halobetasol, betamethasone dipropionate in augmented formulations, diflorasone diacetate in augmented formulations, and fluocinonide at 0.1%, or a potent to a mid-potent corticosteroid, such as betamethasone dipropionate, mometasone furoate, diflorasone diacetate, halcinonide, fluocinonide, and desoximetasone. In some embodiments, the formulation comprises a superpotent corticosteroid. In some embodiments, the formulation comprises a potent to a mid-potent corticosteroid.

Other steroids that are suitable for the formulation of the invention include corticosteroids other than superpotent, potent, or mid-potent corticosteroids. Any corticosteroid that is suitable for topical application to the skin or mucous membrane of a human may be the corticosteroid of the formulation. The benefits of increased efficacy at lower concentration include reduced systemic exposure to the corticosteroid, increased local as well as systemic safety, and reduced cost of materials for making the therapeutic corticosteroid formulation. These benefits are applicable to corticosteroids of any potency, such as a corticosteroid of potency classes 3 to 7, upper mid-strength to least potent. For example desonide gel or foam is a class 6 mild corticosteroid and desonide lotion is a class 5 lower mid-strength corticosteroid. Desonide is widely used in children at a concentration of 0.05%. It is conceived that a formulation containing a concentration of desonide of less than 0.05% in which the potency is similar to that of formulations containing 0.05% desonide would be especially useful in order to reduce the total amount of steroid exposure experienced by children treated with desonide. Thus, included within the present invention are formulations containing concentrations of particular corticosteroids below those shown in Table 1. For example, the invention pertains to concentrations less than 0.005% for fluticasone propionate, concentrations less than 0.01% for fluocinolone acetonide, concentrations less than 0.025% for budesonide, beclomethasone, and triamcinolone acetonide, concentrations less than 0.05% for flurandemolide, desonide, and aclometasone dipropionate, concentrations less than 0.1% for amcinonide, betamethasone valerate, prednicarbate, hydrocortisone butyrate, and hydrocortisone probutate, and concentrations less than 0.2% for hydrocortisone valerate. The invention may also be practiced with any form of a corticosteroid, such as an ester, diester, free alcohol, or acetonide form of a corticosteroid.

In some embodiments, the formulation comprises a superpotent corticosteroid at a concentration less than 0.05% (w/w), e.g., 0.04% or less, 0.035% or less, 0.03% or less, 0.025% or less, 0.02% or less, 0.015% or less, or 0.01% or less. In some embodiments, the formulation comprises clobetasol (e.g., clobetasol propionate) at a concentration less than 0.05% (w/w), e.g., 0.04% or less, 0.035% or less, 0.03% or less, 0.025% or less, 0.02% or less, 0.015% or less, or 0.01% or less. In some embodiments, the formulation comprises betamethasone (e.g., betamethasone dipropionate) at a concentration less than 0.05% (w/w), e.g., 0.04% or less, 0.035% or less, 0.03% or less, 0.025% or less, 0.02% or less, 0.015% or less, or 0.01% or less. In some embodiments, the formulation comprises halobetasol (e.g., halobetasol propionate) at a concentration less than 0.05% (w/w), e.g., 0.04% or less, 0.035% or less, 0.03% or less, 0.025% or less, 0.02% or less, 0.015% or less, or 0.01% or less. In some embodiments, the formulation comprises diflorasone (e.g., diflorasone diacetate) at a concentration less than 0.05% (w/w), e.g., 0.04% or less, 0.035% or less, 0.03% or less, 0.025% or less, 0.02% or less, 0.015% or less, or 0.01% or less.

In some embodiments, the formulation comprises a potent or mid-potent corticosteroid at a concentration less than 0.05% (w/w), e.g., 0.04% or less, 0.035% or less, 0.03% or less, 0.025% or less, 0.02% or less, 0.015% or less, or 0.01% or less. In some embodiments, the formulation comprises betamethasone (e.g., betamethasone dipropionate) at a concentration less than 0.05% (w/w), e.g., 0.04% or less, 0.035% or less, 0.03% or less, 0.025% or less, 0.02% or less, 0.015% or less, or 0.01% or less. In some embodiments, the formulation comprises diflorasone (e.g., diflorasone diacetate) at a concentration less than 0.05% (w/w), e.g., 0.04% or less, 0.035% or less, 0.03% or less, 0.025% or less, 0.02% or less, 0.015% or less, or 0.01% or less. In some embodiments, the formulation comprises desoximetasone at a concentration less than 0.05% (w/w), e.g., 0.04% or less, 0.035% or less, 0.03% or less, 0.025% or less, 0.02% or less, 0.015% or less, or 0.01% or less. In some embodiments, the formulation comprises fluocinonide at a concentration less than 0.05% (w/w), e.g., 0.04% or less, 0.035% or less, 0.03% or less, 0.025% or less, 0.02% or less, 0.015% or less, or 0.01% or less.

In some embodiments, the formulation comprises a superpotent or potent corticosteroid selected from the group consisting of fluocinonide, mometasone furoate, halcinonide, and amcinonide in an amount less than 0.1% (w/w), e.g., 0.09% or less, 0.08%, or less, 0.07% or less, 0.06% or less, 0.05% or less, 0.04% or less, or 0.03% or less.

The concentration of the corticosteroid in the formulation is that which is sufficient to provide an anti-inflammatory response to an area of skin or mucous membrane to which it is applied. The concentration may vary depending on the particular disorder to be treated, the particular corticosteroid utilized, and other parameters.

Because the primary purpose to which the invention is conceived to pertain is to reduce the amount of corticosteroid that is available to enter the systemic circulation following the topical administration of corticosteroids, the preferred concentration of corticosteroid in the formulation of the invention is less than that present in prior art topical formulations containing the same corticosteroid. For example, both clobetasol propionate and halobetasol propionate topical formulations are presently available as creams and ointments in a concentration of 0.05% (w/w). Thus, it is preferred that the concentration of such corticosteroid in the formulation of the present invention is less than 0.05% (w/w). However, concentrations of corticosteroid at the same level, that is at 0.05%, or higher, are not excluded from the scope of the present invention unless indicated as such in the claims.

In some embodiments, the formulation contains a corticosteroid as disclosed in Table 1 in an amount that is less than the amount disclosed for the corticosteroid in Table 1, e.g., at an amount that is 80%, 70%, 60%, 50%, 40%, 30%, 20%, or less than that disclosed in Table 1. For example, for a superpotent or potent corticosteroid in Table 1 such as clobetasol propionate, betamethasone dipropionate, halobetasol propionate, diflorasone diacetate, desoximetasone, or fluocinonide that is disclosed as being available at a concentration of 0.05%, in some embodiments, the formulation of the invention contains a concentration of the superpotent, potent, or mid-potent corticosteroid that is less than 0.05% (w/w), e.g., an amount that is 80%, 70%, 60%, 50%, 40%, 30%, 20%, or less of the 0.05% that is presently available. As another non-limiting example, for a superpotent or potent corticosteroid in Table 1 such as fluocinonide, mometasone furoate, halcinonide, or amcinonide that is disclosed as being available at a concentration of 0.1%, in some embodiments, the formulation of the invention contains a concentration of the superpotent or potent corticosteroid that is less than 0.1% (w/w), e.g., an amount that is 80%, 70%, 60%, 50%, 40%, 30%, 20%, or less of the 0.1% that is presently available.

In a preferred embodiment, the formulation of the invention contains a concentration of the corticosteroid such as clobetasol propionate or halobetasol propionate that is 80% or less than that presently available, that is a concentration of 0.04% or less. In another preferred embodiment, the formulation contains a concentration of the corticosteroid that is 60% or less than that presently available, that is a concentration of 0.03% or less. In another preferred embodiment, the concentration is 50% or less than that presently available, that is a concentration is 0.025% or less. In another preferred embodiment, the formulation of the invention contains a concentration of corticosteroid that is 40% or less than that presently available, that is has a concentration of 0.02% or less. In another preferred embodiment, the formulation contains a concentration of the corticosteroid that is 20% or less than that presently available, that is has a concentration of 0.01% or less. In another preferred embodiment, the concentration of corticosteroid in the formulation of the invention is 10% or less than that presently available, that is 0.005% or less.

Monocarboxylic and Dicarboxylic Acid Esters

In some embodiments, the corticosteroid formulations disclosed herein comprise one or more monocarboxylic acid esters and/or dicarboxylic acid esters. In some embodiments, the formulation comprises a dicarboxylic acid ester. In some embodiments, the formulation comprises a monocarboxylic acid ester. In some embodiments, the formulation comprises a dicarboxylic acid ester and a monocarboxylic acid ester.

In some embodiments, the dicarboxylic acid ester (DCAE) that is suitable for the present invention has the formula $R_1OOC-(CH_2)n-COOR_2$, where $R_1$ and $R_2$ are alkyl groups containing between 1 and 4 carbons or aryl groups and may be the same or may be different and where n is straight or branched and is between 1 and 12. Examples of DCAEs containing one or more aryl groups are dibenzyl esters of dicarboxylic acids. A preferred dicarboxylic acid ester is diethyl sebacate, which has the formula $CH_3CH_2OOC-(CH_2)_8-COOCH_2CH_3$. Diethyl sebacate is considered to be typical of the dicarboxylic acid esters disclosed as each of the parameters $R_1$, $R_2$, and n of diethyl sebacate are approximately in the center of the range of each of the specified parameters.

Examples of other suitable dicarboxylic acid esters where $R_1=R_2$ are dimethyl, diethyl, dipropyl, diisopropyl, dibutyl and diisobutyl esters such as oxalate, malate, succinate, glutarate, adipate, pimelate, suberate, and azalate. Examples of suitable dicarboxylic acid esters where $R_1 \neq R_2$ are methyl ethyl, methyl propyl, methyl butyl, methyl isopropyl, ethyl propyl, ethyl butyl, ethyl isopropyl, and propyl butyl esters such as oxalate, malate, succinate, glutarate, adipate, pimelate, suberate, azalate, and sebacate. In some embodiments, the formulation comprises a dicarboxylic acid ester selected from the group consisting of diethyl sebacate, diisopropyl adipate, and dibutyl sebacate. In some embodiments, the formulation comprises diethyl sebacate.

Alternatively, or in combination with the DCAE, the formulation may contain a monocarboxylic acid ester (MCAE). The MCAE that is suitable for the present invention has the formula $CH_3-(CH_2)_n-COOR_1$, where $R_1$, is an alkyl group containing between 1 and 4 carbons or an aryl group, and where n is straight or branched and is between 1 and 12. Examples of such monocarboxylic acid esters include methyl, ethyl, propyl, isopropyl, butyl, or an aryl such as benzyl formate, acetate, propionate, butyrate, valerate, laurate, myristate, palmitate, and stearate. Examples of preferred monocarboxylic acid esters are isopropyl palmitate and isopropyl myristate. In some embodiments, the formulation comprises a monocarboxylic acid ester selected from the group consisting of isopropyl myristate, isopropyl palmitate, and benzyl benzoate. In some embodiments, the formulation comprises isopropyl myristate.

In some embodiments, the liquid oil component comprises one or more monocarboxylic acid esters and/or dicarboxylic acid esters as disclosed herein and further comprises mineral oil and/or light mineral oil. In some embodiments, the liquid oil component comprises a monocarboxylic acid ester and light mineral oil. In some embodiments, the liquid oil component comprises a dicarboxylic acid ester and light mineral oil.

The concentration of the liquid oil component of the formulation containing a DCAE and/or an MCAE is at least that which is sufficient to dissolve at least 25% of the entire amount of the corticosteroid in the formulation at a room temperature of 22° C. In one embodiment, the concentration of the liquid oil component is sufficient to dissolve between 25% and 50% of the corticosteroid, such as about 40%. In a preferred embodiment, the concentration of the liquid oil component is sufficient to dissolve between 50% and 60% of the corticosteroid, such as about 55%. In another preferred embodiment, the concentration of the liquid oil component is sufficient to dissolve between 60% and 70% of the corticosteroid, such as about 65%. In another preferred embodiment, the concentration of the liquid oil component is sufficient to dissolve between 70% and 80% of the corticosteroid, such as about 75%. In another preferred embodiment, the concentration of the liquid oil component is sufficient to dissolve between 80% and 90% of the corticosteroid, such as about 85%. In another preferred embodiment, the concentration of the liquid oil component is sufficient to dissolve between 90% and 100% of the corticosteroid, such as about 95%. In some embodiments, the corticosteroid is fully solubilized in the liquid oil component.

In a more preferred embodiment, the concentration of the liquid oil component is sufficient to dissolve 100% or more of the corticosteroid in the formulation at a room temperature of 22° C. For example, the concentration of the liquid oil component may be between 1.0 and 1.5 times that which is sufficient to dissolve the entire amount of the corticosteroid in the formulation. For example, the concentration of the liquid oil component may be greater than 1.5 times that which is sufficient to dissolve the entire amount of the corticosteroid in the formulation, such as between 1.5 times and 3.0 times that which is sufficient to dissolve the amount of corticosteroid in the formulation. For example, the concentration of the liquid oil component may be more than 3.0 times that which is sufficient to dissolve the entire amount of the corticosteroid in the formulation. Examples of suitable concentrations of liquid oil component in terms of amount required to dissolve the entire amount of corticosteroid in the formulation at room temperature include 0.25, 0.4, 0.5, 0.75, 1.0, 1.05, 1.15, 1.25, 1.25, 1.24, 1.45, 2.0, 2.5, 3.0, 3.5, 4.0, 4.5, 5.0, 5.5, and 6.0 times or higher than that which is sufficient to dissolve the corticosteroid in the formulation at a room temperature of 22° C. In some embodiments, the concentration of the liquid oil component is between 1.5 and 3 times that required to completely solubilize the amount of corticosteroid in the composition at a temperature of 22° C.±2° C. In some embodiments, the concentration of the liquid oil component is between 1.75 and 2.75 times that required to completely solubilize the amount of corticosteroid in the composition at a temperature of 22° C.±2° C.

The combined concentrations of the DCAE and/or the MCAE in the liquid oil component of the formulation is at least about 5% of the oil component, such as at least 10%, 15%, 20%, 25%, 30%, 40%, 50%, 60%, 70%, 80%, or 90% of the oil component. In some embodiments, the DCAE and/or MCAE constitute at least 15% of the liquid oil component. In some embodiments, the DCAE and/or MCAE constitute at least 20% of the liquid oil component. In some embodiments, the DCAE and/or MCAE constitute at least 25% of the liquid oil component. In one embodiment, the DCAE, and MCAE if present, constitute 100% of the liquid oil component of the formulation.

Formulation and Additional Components

The corticosteroid composition of the present invention may be any formulation that incorporates DCAE and/or MCAE such as foams and emulsions including creams and lotions. Preferably, the formulation is an emulsion in which an internal oil component is dispersed within an external aqueous phase or an internal aqueous phase is dispersed within an external oil component. Examples of emulsions include water-in-oil, oil-in water, water-in-oil-in-water emulsion, and oil-in-water-in-oil emulsions. In some embodiments, the emulsion is a macroemulsion, a microemulsion, or a nanoemulsion. Also contemplated is a liposomal dispersion in which, preferably, the DCAE and/or MCAE is incorporated in the lipid component of the liposomes. Also contemplated are other formulations in which non-polar and polar liquid ingredients coexist with the formulation.

Preferably, the formulation of the invention contains a thickening agent to provide viscosity so that the formulation may be provided in the form of a lotion or cream. Preferably but not necessarily, the thickening agent is miscible or soluble in an aqueous fluid. Examples of suitable thickening agents include acacia, alginic acid, bentonite, carbomers, also known as carboxy vinyl polymers, such as sold under the tradename Carbopol® (Lubrizol, Wickliffe, Ohio), carboxymethylcellulose, ethylcellulose, gelatin, hydroxyethylcellulose, hydroxypropyl cellulose, magnesium aluminum silicate, methylcellulose, poloxamers, polyvinyl alcohol, sodium alginate, tragacanth, and xanthan gum. The thickening agent may also reside in the oil or lipophilic portion of the formulation. Examples of suitable lipophilic thickening agents include cetyl alcohol, stearyl alcohol, glyceryl stearate, white beeswax, microcrystalline wax, hydrogenated polyisobutane polymers, and emulsifying wax.

If desired or required in order to obtain the form of the formulation desired, a surfactant or emulsifier may be included. The emulsifier is preferably a non-ionic emulsifier such as a sorbitan ester, a polyoxyethylene derivative of a sorbitan ester or a glyceryl ester; a polymeric emulsifier such as a acrylates/C10-C30 alkyl acrylate crosspolymer such as those sold under the tradename PEMULEN® (The Lubrizol Corporation, Wickliffe, Ohio); or an anionic emulsifier such as an alkali soap such as sodium or potassium oleate, an amine soap such as triethanolamine stearate, a detergent such as sodium lauryl sulfate, sodium dioctyl sulfosuccinate, and sodium docusate. Less preferred are cationic emulsifiers such as quaternary ammonium salts. Particular examples of suitable anionic and non-ionic emulsifiers include glyceryl monostearate, polyoxyethylene monooleate, polyoxyethylene monostearate, polyoxyethylene monolaurate, potassium oleate, sodium lauryl sulfate, sodium oleate, sorbitan monolaurate, sorbitan monopalmitate, sorbitan monostearate, sorbitan tristearate, sorbitan monooleate, sorbitan trioleate, triethanolamine oleate, polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate, and polyoxyethylene sorbitan trioleate.

The formulation may contain other pharmaceutically acceptable excipients. Preferably, the formulation contains a humectant such as glycerin, sorbitol, hexylene glycol, urea, or propylene glycol. Preferably, the formulation contains an emollient such as petrolatum, lanolin, mineral oil, light mineral oil, stearic acid, cyclomethicone, or dimethicone. Additional optional excipients include stabilizers, preservatives such as methylparaben or benzyl alcohol, pH adjusting agents such as sodium hydroxide, chelating agents such as EDTA and its salts, and buffers.

The formulation may include other lipophilic liquids in an amount that is sufficient to be miscible with the dicarboxylic acid ester and/or monocarboxylic acid ester. The lipophilic liquid may be an emollient such as lanolin oil, mineral oil, light mineral oil, isostearic acid, squalene, octyldodecanol, castor oil, fractionated coconut oil, cyclomethicone, or dimethicone.

The formulation of the invention may be made by any method known to make a uniphase or multiphase pharmaceutical formulation for topical administration. In some embodiments, the formulation is made as described in the Examples section below. In order to make a multiphase formulation such as an emulsion, for example, the components of the aqueous phase and of the oil phase may be separately combined and mixed until homogenous solutions are obtained and then the aqueous solution and the oil solution may be combined and mixed, such as by shear mixing, to form the formulation. The oil phase may be added to the water phase, or the water phase may be added to the oil phase. The phases may be combined and mixed, such as at elevated temperatures of 50-90° C. or at room temperature, that is between 20-30° C., or at a temperature between room temperature and the elevated temperatures.

Methods of Treatment

The formulation may be used for topical treatment or prophylaxis of a dermatological or mucosal disorder or condition that is responsive to the application of topical corticosteroids. Examples of such disorders or conditions include but are not limited to psoriasis (e.g., plaque psoriasis, guttate psoriasis, inverse psoriasis, pustular psoriasis, erythrodermic psoriasis, nail psoriasis, or psoriatic arthritis), dermatitis such as atopic, contact, or hand dermatitis, eczema, seborrheic dermatitis, rash, lichen planus, lichen sclerosus, and poison ivy dermatitis. In some embodiments, a corticosteroid composition as described herein is used for a method of treating psoriasis. In some embodiments, a corticosteroid composition as described herein is used for a method of treating plaque psoriasis. In some embodiments, a corticosteroid composition as described herein is used for a method of treating mild to moderate plaque psoriasis. In some embodiments, a corticosteroid composition as described herein is used for a method of treating moderate to severe plaque psoriasis.

In some embodiments, a corticosteroid as described herein (e.g., clobetasol propionate, betamethasone dipropionate, diflorasone diacetate, or desoximetasone at a concentration less than 0.05%) is used in the manufacture of a medicament for the treatment of a condition that is responsive to the application of topical corticosteroids. In some embodiments, the corticosteroid is formulated in a liquid oil component as described herein (e.g., a liquid oil component that includes a dicarboxylic acid ester and/or a monocarboxylic acid ester, and optionally mineral oil and/or light mineral oil). In some embodiments, the medicament is for the treatment of psoriasis (e.g., plaque psoriasis, guttate psoriasis, inverse psoriasis, pustular psoriasis, erythrodermic psoriasis, nail psoriasis, or psoriatic arthritis), dermatitis such as atopic, contact, or hand dermatitis, eczema, seborrheic dermatitis, rash, or poison ivy dermatitis.

The formulation of the invention maintains a VCA score as high or that is similar to the VCA score that is obtained by the application of prior art formulations containing higher concentrations of the corticosteroid, such as the superpotent corticosteroid. Because the VCA score is determinative of local efficacy, the formulation of the invention, even at greatly reduced concentrations of corticosteroid, would be understood by one of skill in the art to be generally as effective locally in the skin as presently available formulations containing higher concentrations of corticosteroid. Additionally, because of the reduced concentration of corticosteroid in the formulation compared to that in the prior art compositions and the concomitant reduction in amount of corticosteroid that is available to enter the systemic circulation upon topical administration of the formulation, it is conceived that the formulation may have similar efficacy but improved safety compared to prior art formulations that contain higher concentrations of corticosteroid. Thus the formulations of this application have particular utility in infants and children in treating skin diseases such as atopic dermatitis and in both adults and children for treating recalcitrant or chronic skin diseases such as psoriasis. It is conceived that the present invention provides an equivalent or better efficacy in treating steroid responsive skin diseases compared to that produced by presently available topical formulations, and with potentially reduced local and systemic side effects.

In some embodiments, a corticosteroid formulation as disclosed herein (e.g., a composition comprising a superpotent, potent, or mid-potent corticosteroid in a liquid oil component comprising one or more MCAEs and/or DCAEs) is administered to a subject in need thereof (e.g., an individual having a dermatological or mucosal disorder or condition such as psoriasis, plaque psoriasis, atopic dermatitis, contact dermatitis, hand dermatitis, eczema, seborrheic dermatitis, rash, or poison ivy dermatitis) for at least 1, 2, 3, 4, 5, 6, or 7 days or longer, e.g., for at least 1, 2, 3, 4, 5, 6, 7, 8, 9, or 10 weeks or longer. In some embodiments, a corticosteroid composition as disclosed herein is administered to a subject in need thereof for a period of 1-30 days, e.g., 7-30 days, 7-28 days, 7-21 days, 7-14 days, 10-30 days, 14-30 days, or 14-28 days. In some embodiments, a corticosteroid composition as disclosed herein is administered to a subject in need thereof for a period of 1-12 weeks, e.g., 1-10, 1-8, 2-12, 2-10, 2-8, 4-12, 4-8, 6-12, or 8-12 weeks.

In some embodiments, a corticosteroid formulation as disclosed herein (e.g., a composition comprising a superpotent, potent, or mid-potent corticosteroid in a liquid oil component comprising one or more MCAEs and/or DCAEs) is administered to a subject in need thereof for a period of treatment equal to or longer than 2 weeks, longer than 3 weeks, longer than 4 weeks, longer than 1 month, longer than 2 months, longer than 3 months, longer than 4 months, longer than 5 months, or longer than 6 months. In some embodiments, a corticosteroid formulation as disclosed herein is administered to a subject in need thereof for a period of treatment up to 2 weeks, up to 3 weeks, up to 4 weeks, up to 1 month, up to 2 months, up to 3 months, up to 4 months, up to 5 months, or up to 6 months. In some embodiments, a corticosteroid formulation as disclosed herein until clearance of the dermatological or mucosal disorder or condition (e.g., psoriasis, dermatitis, or rash) is achieved. In some embodiments, the corticosteroid formulation is applied to the affected area or areas of skin one, two, or three times a day. In some embodiments, the corticosteroid formulation is applied to the affected area or areas of skin once daily. In some embodiments, the corticosteroid formulation is applied to the affected area or areas of skin twice daily. In some embodiments, the corticosteroid formulation is applied to the affected area or areas of skin up to two, three, or four times a day.

In some embodiments, a corticosteroid formulation as disclosed herein (e.g., a composition comprising a superpotent, potent, or mid-potent corticosteroid in a liquid oil component comprising one or more MCAEs and/or DCAEs) is administered to a subject in need thereof in two or more treatment periods, in which the treatment periods are separated by a period of time in which the corticosteroid composition is not administered. For example, in some embodiments, a first treatment period is administered for a period of 1, 2, 3, 4, 5, 6, or 7 days or longer, e.g., least 1, 2, 3, 4, 5, 6, 7, 8, 9, or 10 weeks or longer, then treatment is stopped for at least 1, 2, 3, 4, 5, 6, or 7 days or longer (e.g., for at least 1, 2, 3, 4, 5 weeks or longer) before the second treatment period (e.g., a period of 1, 2, 3, 4, 5, 6, or 7 days or longer, e.g., least 1, 2, 3, 4, 5, 6, 7, 8, 9, or 10 weeks or longer) is administered.

In some embodiments, a corticosteroid formulation as disclosed herein (e.g., a composition comprising a superpotent, potent, or mid-potent corticosteroid in a liquid oil component comprising one or more MCAEs and/or DCAEs) is administered to a subject in need thereof in combination with one or more other therapies for the dermatological or mucosal disorder or condition. For example, in some embodiments, a corticosteroid formulation as disclosed herein is administered in combination with phototherapy. In some embodiments, a corticosteroid formulation as disclosed herein is administered in combination with a medication such as a TNF-alpha inhibitor (e.g., infliximab, etanercept, adalimumab, or golimumab), an interleukin inhibitor (e.g., an IL-17 inhibitor, IL-23 inhibitor, IL-12/23 inhibitor), a T cell inhibitor), a protein kinase C inhibitor (e.g., AEB071), a mitogen-activated protein kinase inhibitor (e.g., BMS-582949), a FMS-like tyrosine kinase inhibitor (e.g., lestaurtinib), a Janus kinase inhibitor tofacitinib, ASP-015K, or INCB018424), a phosphodiesterase 4 inhibitor (e.g., apremilast, AN2728, or MK0873), a nerve growth factor inhibitor (e.g., CF101), an anti-folate agent (e.g., methotrexate, aminopterin, or BCX-4208), a calcineurin inhibitor (e.g., cyclosporine), an anti-angiogenic agent (e.g., anti-VEGF antibody or soluble VEGFR), a vitamin D analog or derivative, or a member of the acetylenic class of retinoids (e.g., tazarotene). In some embodiments, the corticosteroid formulation and the other therapy are administered at the same time or substantially the same time. In some embodiments, the corticosteroid formulation and the other therapy are administered at different times.

In some embodiments, a corticosteroid formulation as disclosed herein is administered to an adult subject. In some embodiments, a corticosteroid formulation as disclosed herein is administered to a juvenile subject.

EXAMPLES

The invention is further illustrated in the following non-limiting examples. In some of the examples, halobetasol propionate is utilized as an exemplary superpotent corticosteroid and diethyl sebacate is utilized as an exemplary dicarboxylic acid ester. It is understood, however, that halobetasol propionate is illustrative of the superpotent, potent, and mid-potent corticosteroids, that diethyl sebacate is illustrative of the DCAE, and that isopropyl myristate is illustrative of the MCAE, and that any corticosteroid, especially a mid-potent, potent, or superpotent corticosteroid, DCAE, or MCAE may be substituted for the illustrated halobetasol propionate, diethyl sebacate, and/or isopropyl myristate with similar results.

Example 1—Formulations

The following formulations as shown in Table 2 were made containing the superpotent corticosteroid halobetasol as halobetasol propionate (HP). Formulations A to D are formulations of the invention. Formulation E is a formulation that is not within the scope of the present invention.

TABLE 2

Corticosteroid Formulations

| | Formulation | | | | |
|---|---|---|---|---|---|
| | A | B | C | D | E |
| Ingredients | | | % w/w | | |
| Halobetasol Propionate (corticosteroid) | 0.035 | 0.025 | 0.01 | 0.035 | 0.035 |
| Diethyl Sebacate (DCAE) | 3.0 | 2.1 | 0.8 | 0.9 | — |
| Isopropyl Myristate (MCAE) | — | — | — | 11.0 | — |
| Light Mineral Oil | 1.0 | 0.7 | 0.3 | — | — |
| Medium Chain Triglycerides | — | — | — | — | 18.0 |
| White Petrolatum | — | — | — | — | 2.0 |
| Butylated Hydroxytoluene | — | — | — | — | 0.01 |
| Sorbitan Monooleate | 0.1 | 0.1 | 0.1 | 0.1 | — |
| Cholesterol | — | — | — | — | 0.5 |
| Stearyl Alcohol | — | — | — | — | 1.0 |
| Cetyl Alcohol | — | — | — | — | 0.5 |
| Propylene Glycol | 7.5 | 7.5 | 7.5 | 7.5 | 7.5 |
| Disodium Edetate Dihydrate | 0.05 | 0.05 | 0.05 | 0.05 | 0.05 |
| Pemulen ® TR-1 | 0.40 | 0.40 | 0.40 | 0.40 | 0.40 |
| Carbopol ® 981 | 0.60 | 0.60 | 0.60 | 0.60 | 0.60 |
| Methylparaben | 0.17 | 0.17 | 0.17 | 0.17 | 0.17 |
| Propylparaben | 0.03 | 0.03 | 0.03 | 0.03 | 0.03 |
| Sodium Hydroxide | q.s. pH 6.0 +/− 1 | | | | |
| Purified Water | q.s.ad 100 | | | | |

Example 2—Determination of Saturation Solubility and Degree of Saturation

The saturation solubility of halobetasol propionate in each of formulations A to D of Example 1 was determined as follows. At a temperatures of 22°+/−2° C., samples containing halobetasol in the liquid oil component components of formulations A to D, respectively, were prepared and stored in glass vials. The samples were shaken at 395 to 405 oscillations/minute for approximately 72 hours using a Burrell WRIST-ACTION® Shaker Model 75 (Burrell Scientific, Pittsburgh, PA). Samples were then centrifuged for 40 minutes at 3500 rpm and the supernatant was collected. The supernatant was filtered using 0.45 um PTFE ACRODISC® Pall syringe filter (Pall Corporation, Port Washington, NY). The filtered samples were analyzed by HPLC using a reverse phase column monitored at 254 nm UV detection. The degree of unsaturation of halobetasol propionate of each formulation was then calculated by multiplying the concentration (% w/w) of the liquid oil component by the saturation solubility of halobetasol in the liquid oil component components and dividing by the concentration of halobetasol propionate in the formulation. The data is shown below in Table 3.

TABLE 3

Saturation Solubility of Corticosteroid Formulations

| Formulation | Concentration of Liquid Oil component (% w/w) | Saturation Solubility (% w/w) | Degree of Unsaturation |
|---|---|---|---|
| A | 4 | 2.41 | 2.8 |
| B | 2.8 | 2.41 | 2.7 |
| C | 1.1 | 2.41 | 2.5 |
| D | 11.9 | 0.45 | 1.5 |

Example 3—Determination of VCA Scores

The mean VCA score of each of the formulations of Example 1 was determined as described in Dow, U.S. Pat. No. 7,300,669 and was assigned a semi-quantitative subjective evaluation score on a scale of 0 to 4. The mean VCA score of a formulation corresponding to that of the commercial product Ultravate® 0.05%; NDC 0072-1400-50 (Bristol-Meyers Squibb Company, Princeton, NJ) was also determined. In contrast to the other formulations tested, Ultravate contains halobetasol propionate at a concentration of 0.05%. In determining the mean VCA score, the evaluator was blinded as to the formulation being tested. The results are shown in Table 4.

TABLE 4

VCA Scores for Corticosteroid Formulations

| Formulation | HP Conc (% w/w) | VCA Mean Score |
|---|---|---|
| A | 0.035 | 2.37 |
| B | 0.025 | 2.40 |
| C | 0.010 | 2.47 |
| D | 0.035 | 2.43 |
| E | 0.035 | 1.77 |
| Ultravate ® | 0.050 | 2.37 |

As shown in Table 4, each of the formulations A to D of the present invention provided a VCA score similar to that of the prior art formulation Ultravate®. This high level of VCA score, which is indicative of the local desired response of the corticosteroid, was obtained even though the level of corticosteroid in the formulations of the invention are markedly lower than that in the prior art formulation. Formulation E, which contained the same concentration of corticosteroid as in Formulations A and D, had a markedly lower VCA score.

Example 4—Formulations

Formulations 4A and 4B of the present invention contain the ingredients shown in Table 5 below. These formulations may be made as follows.

A separate aqueous phase is made. In a manufacturing vessel, purified water and disodium edetate dihydrate are combined and the mixture is agitated until a clear solution is achieved. Sorbitol and/or propylene glycol, methylparaben, and propylparaben are then added to the mixture. The mixture is continuously mixed and is heated to approximately 75° C. The mixture is agitated until a solution is obtained. The mixture is then removed from the heat source and allowed to cool to below 40° C. with continued mixing. With continuous propeller agitation Carbopol 981 and Pemulen TR-1 are added to the mixture and dispersed. The propeller mixing is continued until the polymers are fully dispersed and hydrated.

A separate oil phase is made. In a vessel diethyl sebacate and halobetasol propionate are combined. The mixture is agitated until a solution is achieved. With continuous propeller mixing, light mineral oil and sorbitan monooleate are added. Mixing is continued until a solution is obtained.

In a separate vessel, a 1N solution of sodium hydroxide is prepared.

With high speed rotor-stator mixing, the oil phase containing the drug (halobetasol propionate) is added to the aqueous phase. Mixing is continued until a homogeneous emulsion is obtained. Propeller mixing is then used in place of the high speed rotor-stator mixing. With continuous mixing an appropriate amount of the sodium hydroxide solution is added incrementally to obtain a pH of 5.5±0.5. Propeller mixing is continued until a homogeneous lotion is obtained.

TABLE 5

Corticosteroid Formulations 4A and 4B

| Ingredients | % w/w | |
|---|---|---|
| | Formula 4A | Formula 4B |
| Halobetasol Propionate | 0.01 | 0.025 |
| Diethyl Sebacate | 2.97 | 2.90 |
| Light Mineral Oil | 8.03 | 2.90 |
| Sorbitan Monooleate | 0.10 | 0.10 |
| Sorbitol Solution, 70% | 10.7 | 10.7 |
| Disodium Edetate, Dihydrate | 0.05 | 0.05 |
| Pemulen TR-1 | 0.40 | 0.40 |
| Carbopol 981 | 0.60 | 0.60 |
| Methylparaben | 0.17 | 0.17 |
| Propylparaben | 0.03 | 0.03 |
| Sodium Hydroxide, q.s. | pH 4.0-6.0 | pH 4.0-6.0 |
| Purified Water, q.s. ad | 100 | 100 |

Example 5—Stability Data

A lotion formulation was made by the method of Example 4 using the ingredients listed in Table 6.

TABLE 6

Halobetasol Lotion Formulation

| Ingredients | Percent w/w |
|---|---|
| Halobetasol propionate (HP) | 0.025 |
| Diethyl Sebacate | 2.10 |
| Light Mineral Oil | 0.70 |
| Sorbitan Monooleate | 0.10 |
| Propylene Glycol | 7.50 |
| Methylparaben | 0.17 |
| Propylparaben | 0.03 |
| Edetate Disodium, Dihydrate | 0.05 |
| Pemulen TR-1 | 0.40 |
| Carbopol 981 | 0.60 |
| Sodium Hydroxide | q.s. ad pH 5.0 |
| Purified Water | q.s. ad 100 |

Halobetasol formulations were tested for physical and chemical stability as shown in Tables 8 and 9 below. The stability specifications for the halobetasol lotion that would be required for a commercial product would typically be as shown in Table 7.

TABLE 7

Stability Specifications

| PARAMETER | FDA REQUIREMENT |
|---|---|
| Description | no substantial change |
| pH | 4.0 to 6.5 |
| Viscosity | 3,000 to 21,000 cps |
| HP Content | 90 to 110% of labeled amount |

For the results shown in Table 8, the formulation was packaged in glass screw-cap jars and tested for stability at refrigerator temperature (5° C.), room temperature (25° C.), and accelerated temperature (40° C.) and tested at the beginning of the study and periodically for up to 6 months. The Description was performed by visual observation, pH was measured with a calibrated pH meter, and viscosity was measured with a Brookfield rotational viscometer using spindle 27 and a speed of 12 rpm. The content of halobetasol propionate was determined by reverse phase HPLC using a C18 column and UV detection.

TABLE 8

Physical and Chemical Stability Results for Halobetasol Formulation (up to 6 months)

| Condition | Time | Description | pH | Viscosity (cps) | HP Content (% of labeled amount) |
|---|---|---|---|---|---|
| Initial | 0 months | White to off-White Lotion | 5.1 | 10,833 | 99.4 |
| 5° C. | 6 months | Conforms | 5.1 | 12,285 | 94.0 |
| 25° C. | 3 months | | 5.1 | 12,140 | 95.3 |
| | 6 months | | 5.1 | 13,215 | 92.1 |
| 40° C. | 1 month | | 5.1 | 12,090 | 95.1 |
| | 3 months | | 5.1 | 12,090 | 93.4 |
| | 6 months | | 5.1 | 12,070 | 92.5 |

For the results shown in Table 9, the formulation was packaged in phenolic lined aluminum tubes and tested for stability at control room temperature (25° C./60% RH), and at accelerated temperatures (30° C./65% RH, 40° C./75% RH) and tested at the beginning of the study and periodically for up to 24 months. The Description was performed by visual observation, pH was measured with a calibrated pH meter, and viscosity was measured with a Brookfield rotational viscometer using spindle 27 and a speed of 12 rpm. The content of halobetasol propionate was determined by reverse phase HPLC using a C18 column and UV detection.

TABLE 8

Physical and Chemical Stability Results for Halobetasol Formulation (up to 24 months)

| Condition | Time | Description | pH | Viscosity (cps) | HP Content (% of labeled amount) |
|---|---|---|---|---|---|
| Initial | 0 months | White to off-White Lotion | 5.4 | 11,132 | 99.5 |
| 25° C./60% RH | 3 months | Conforms | 5.4 | 10,938 | 98.8 |
| | 6 months | | 5.3 | 11,146 | 96.0 |
| | 9 months | | 5.4 | 10,833 | 99.5 |
| | 12 months | | 5.4 | 10,625 | 99.3 |
| | 18 months | | 5.4 | 11,063 | 99.4 |
| | 24 months | | 5.4 | 10,625 | 99.8 |

TABLE 8-continued

Physical and Chemical Stability Results for
Halobetasol Formulation (up to 24 months)

| Condition | Time | Description | pH | Viscosity (cps) | HP Content (% of labeled amount) |
|---|---|---|---|---|---|
| 30° C./65% RH | 3 months | | 5.3 | 11,333 | 99.2 |
| | 6 months | | 5.3 | 10,854 | 98.5 |
| | 9 months | | 5.3 | 10,667 | 99.5 |
| | 12 months | | 5.2 | 10,500 | 97.4 |
| 40° C./75% RH | 1 month | | 5.3 | 11,250 | 98.2 |
| | 3 months | | 5.3 | 11,229 | 98.2 |
| | 6 months | | 5.4 | 10,750 | 94.4 |

The HP lotion was determined to be within the typical specifications at all test times. The data of Table 8 and Table 9 indicates that this formulation product would be expected to have a minimum of 2 year shelf life at room temperature based on the favorable results.

Example 6—Relative Therapeutic Potency of Topical Corticosteroid Compositions Via Visual Assessment of Vasoconstriction Properties The therapeutic potency of several superpotent, potent, and mid-potent corticosteroids prepared according to the methods described herein, relative to commercially available corticosteroid compositions, was evaluated in a vasoconstrictor assay. Formulations comprising clobetasol propionate at a concentration of 0.03% (w/w) or 0.01% (w/w), betamethasone dipropionate at a concentration of 0.03% (w/w), desoximetasone at a concentration of 0.03% (w/w), or diflorasone diacetate at a concentration of 0.03% (w/w) were prepared as lotion formulations. The composition of each corticosteroid formulation is presented below in Table 10. The compositions were prepared substantially as described in Example 4 above.

Two reference compositions were used as comparators. The first reference composition (also referred to herein as "Formulation I") was a superpotent corticosteroid formulation, Clobex® (clobetasol propionate lotion, 0.05%, Galderma Laboratories, L.P., Fort Worth, TX). The second reference composition (also referred to herein as "Formulation J") was a potent corticosteroid formulation, Topicort® (desoximetasone gel, 0.05%, Valeant Canada LP/Valeant Canada S.E.C.).

Using a four-point ordinal visual scale ranging from 0 (no pallor) to 3 (intense pallor), the relative therapeutic potency of each of Formulations A-H were evaluated and compared to the reference formulations (Formulations I and J). A randomized, evaluator-blinded, within-subject, single-center vasoconstrictor study to determine their relative therapeutic potency under non-occluded conditions in 29 healthy adult subjects. A 10 μL amount of each formulation was applied to a single application site on the flexor surfaces of each subject's ventral forearms (left and right) and left in place for 16 hours. The 16 hour dose-duration treatment is preferred by the FDA to determine the relative potency of new topical corticosteroids and allows enough time for the lowest potency products to maximize skin blanching. The degree of vasoconstriction was measured using visual scoring at pre-dose and at approximately 18 hours after the application of the formulations (approximately 2 hours after washing of the test sites to remove study drug), using the following rating scale: 0=no pallor (no change from surrounding area); 1=mild pallor (slight or indistinct outline of application site); 2=moderate pallor (discernible outline of application site); 3=intense pallor (clean, distinct outline of application site).

The mean visual assessments from the study, in order of most to least potent formulations, are presented in Table 11 below.

TABLE 10

Corticosteroid Formula Compositions

| Ingredients | Formulation | | | | | | | |
|---|---|---|---|---|---|---|---|---|
| | A | B | C | D | E | F | G | H |
| | % w/w | | | | | | | |
| Clobetasol propionate | 0.03 | 0.03 | 0.01 | — | — | — | 0.03 | 0.03 |
| Betamethasone dipropionate | — | — | — | 0.03 | — | — | — | — |
| Desoximetasone | — | — | — | — | 0.03 | — | — | — |
| Diflorasone diacetate | — | — | — | — | — | 0.03 | — | — |
| Diethyl sebacate | 2.01 | 5.35 | 0.64 | 2.10 | 3.74 | 3.87 | 2.94 | — |
| Light mineral oil | 0.74 | 1.98 | 0.24 | 0.78 | 1.39 | 1.43 | 2.94 | — |
| Isopropyl myristate | — | — | — | — | — | — | — | 13.88 |
| Propylene glycol (PG) | 7.50 | 7.50 | 7.50 | 7.50 | 7.50 | 7.50 | 7.50 | 7.50 |
| Sorbitol solution, 70% | — | — | — | — | — | — | — | — |
| Disodium edatate dihydrate | 0.05 | 0.05 | 0.05 | 0.05 | 0.05 | 0.05 | 0.05 | 0.05 |
| Benzyl alcohol | 0.90 | 0.90 | 0.90 | 0.90 | 0.90 | 0.90 | 0.90 | 0.90 |
| Sorbitan monooleate | 0.10 | 0.10 | 0.10 | 0.10 | 0.10 | 0.10 | 0.10 | 0.10 |
| Pemulant TR-1 (carbomer copolymer type B) | 0.40 | 0.40 | 0.40 | 0.40 | 0.40 | 0.40 | 0.40 | 0.40 |
| Carbopol 981 (carbomer homopolymer type A) | 0.60 | 0.60 | 0.60 | 0.60 | 0.60 | 0.60 | 0.60 | 0.60 |
| Sodium hydroxide | 0.25 | 0.25 | 0.25 | 0.25 | 0.25 | 0.25 | 0.25 | 0.25 |
| Purified water | 87.42 | 82.84 | 89.31 | 87.29 | 85.04 | 84.87 | 84.29 | 76.29 |

TABLE 11

Mean Results From Visual Assessments in Order of Most to Least Potent Formulations

| Formulation | N | Mean and Standard Deviation | REGWQ Grouping* |
|---|---|---|---|
| Formulation G | 29 | 1.8276 ± 0.5223 | A |
| Formulation A | 29 | 1.7759 ± 0.4741 | A, B |
| Formulation H | 29 | 1.7241 ± 0.5276 | A, B |
| Formulation I | 29 | 1.7069 ± 0.4913 | A, B |
| Formulation B | 29 | 1.6552 ± 0.5992 | A, B |
| Formulation C | 29 | 1.6379 ± 0.6109 | A, B |
| Formulation D | 29 | 1.6207 ± 0.4562 | A, B |
| Formulation F | 29 | 1.5517 ± 0.4882 | B, C |
| Formulation J | 29 | 1.4138 ± 0.6953 | C, D |
| Formulation E | 29 | 1.3276 ± 0.6164 | D |

*Products with the same Ryan-Einot-Gabriel-Welsh Multiple Range Test (REGWQ) grouping letter are not statistically significantly different using a global 5% significance level.

These results show that the formulations with the greatest and least blanching were Formulations G and E, respectively. Based on the overall visual data results from the REGWQ tests, the corticosteroid formulations of Table 9 can be classified as follows:

Formulations A, B, G, and H were comparable to reference Formulation I (a known "superpotent" formulation, and can be classified as super potent topical corticosteroid formulations (Class I);

Formulations C, D, and F can potentially be classified as super potent and at least as high potent corticosteroid formulations (Class I-II); and Formulation E can potentially be classified as a high potent corticosteroid formulation and at least as an "upper mid-strength" corticosteroid formulation (Class II-III).

In conclusion, the superpotent, high potent, and mid-potent corticosteroid formulations evaluated herein exhibit comparable vasoconstriction properties as known corticosteroid compositions having a significantly higher concentration of corticosteroid (0.05%).

The data presented herein demonstrate that by formulating a corticosteroid in a liquid oil component comprising a dicarboxylic acid ester and/or monocarboxylic acid ester, a reduced concentration of corticosteroid can be used while maintaining comparable potency to formulations having a relatively higher concentration of corticosteroid. For example, for the corticosteroid clobetasol propionate, clobetasol propionate in an amount of 0.03% formulated as described herein exhibits comparable potency and can be classified in the same category of corticosteroids (Class I) as a currently available 0.05% clobetasol propionate lotion, even though the clobetasol propionate formulation of the disclosure has 40% less clobetasol propionate than the currently available clobetasol propionate lotion. Furthermore, a formulation comprising only 20% of the amount of clobetabol propionate as the currently available lotion (i.e., 0.01% clobetasol propionate) exhibits a level of potency in the range of Class I-II corticosteroids.

It is known by persons skilled in the art that the vehicle by which a corticosteroid is delivered can affect the potency of the corticosteroid formulation. Typically, occlusive (ointment), alcoholic, and/or propylene glycol type vehicles tend to generate higher vasoconstriction responses than aqueous base vehicles such as emulsions, gels, and solutions. Thus, a corticosteroid at a specified amount that is formulated as an ointment is often more potent than the same amount of corticosteroid formulated as a gel, a cream, or lotion, due to the occlusive nature of the ointment that improves absorption of the corticosteroid. See, Uva et al., *Int J Endocrinol*, 2012, 2012:561018. However, ointments tend to be greasy, which can result in poor patient satisfaction and compliance. Therefore, it is desirable to develop formulations that have higher patient satisfaction and compliance and that still maintain comparable potency to formulation vehicles that are traditionally associated with relatively higher potency.

As disclosed herein, the corticosteroid compositions of the invention can be formulated in different forms, including as lotions and creams, in order to address patient satisfaction and compliance, while maintaining comparable potency to formulations that tend to generate higher vasoconstriction responses. For example, the 0.03% betamethasone dipropionate lotion of Formulation D can potentially be classified as a Class I corticosteroid and at least as a Class II corticosteroid. This level of potency that is achieved with Formulation D is at least comparable to non-augmented betamethasone dipropionate 0.05% ointment (trade name Diprosone®), which is classified as a Class II corticosteroid, despite Formulation D having 40% less betamethasone dipropionate than Diprosone®. Furthermore, the 0.03% betamethasone dipropionate lotion of Formulation D is nearly as potent as augmented betamethasone dipropionate 0.05% ointment (Diprolene®), which is classified as a Class I "superpotent" corticosteroid, despite Formulation D having 40% less betamethasone dipropionate than Diprolene®.

As another example, for desoximetasone, a desoximetasone 0.05% gel formulation (Topicort®, which has an alcohol-containing vehicle) is classified as a Class II "potent" corticosteroid while a desoximetasone 0.05% cream formulation is classified as a Class III "intermediate potent" corticosteroid. The data presented herein demonstrate that a 0.03% desoximetasone lotion (Formulation E) can potentially be classified as a high potent corticosteroid formulation (Class II) and can at least be classified as an "upper mid-strength" corticosteroid formulation (Class III). Thus, the lotion formulation of Formulation E can potentially be classified as the same level of potency as a 0.05% gel formulation of desoximetasone (reference Formulation J), despite having 40% less desoximetasone than the Topicort® gel formulation. Formulation E is also at least as potent as a Class III desoximetasone 0.05% cream formulation, despite Formulation E having 40% less desoximetasone.

For the corticosteroid diflorasone diacetate, a 0.05% cream formulation (Psorcon®) is classified as a Class II "potent" corticosteroid. The data presented herein demonstrate that a 0.03% diflorasone diacetate lotion (Formulation F) can potentially be classified as a high potent corticosteroid formulation (Class II) and can at least be classified as an "upper mid-strength" corticosteroid formulation (Class III). Thus, the lotion formulation of Formulation F can potentially be classified as the same level of potency as a 0.05% cream formulation of diflorasone diacetate, despite having 40% less diflorasone diacetate than the cream formulation.

Further modifications, uses, and applications of the invention described herein will be apparent to those skilled in the art. It is intended that such modifications be encompassed in the following claims.

What is claimed is:

1. A method of treating a dermatological or mucosal disorder or condition, the method comprising topically administering a pharmaceutical composition comprising a corticosteroid to the skin of an individual having the dermatological or mucosal disorder or condition, wherein the pharmaceutical composition comprises:

a liquid oil component comprising one or more monocarboxylic acid esters and/or dicarboxylic acid esters, and mineral oil, light mineral oil, or a combination thereof, and a corticosteroid at a concentration of about 0.01% to about 0.030% or less, and wherein at least 25% of the corticosteroid is solubilized in the liquid oil component at a temperature of 22° C.+/−2° C.; and an aqueous component comprising water;

wherein the corticosteroid is selected from the group consisting of clobetasol propionate, betamethasone dipropionate, halobetasol propionate, diflorasone diacetate, desoximetasone, mometasone furoate, betamethasone valerate, halcinonide, budesonide, fluocinonide, and amcinonide; and wherein the pharmaceutical composition is free of white petrolatum;

wherein the pharmaceutical composition is formulated as a lotion or a cream.

2. The method of claim 1, wherein the corticosteroid is halobetasol propionate.

3. The method of claim 2, wherein the concentration of the corticosteroid is about 0.03%.

4. The method of claim 1, wherein the concentration of the corticosteroid is about 0.01%.

5. The method of claim 1, wherein the liquid oil component comprises a dicarboxylic acid ester.

6. The method of claim 5, wherein the dicarboxylic acid ester is diethyl sebacate.

7. The method of claim 1, wherein the liquid oil component comprises a monocarboxylic acid ester.

8. The method of claim 7, wherein the monocarboxylic acid ester is isopropyl myristate.

9. The method of claim 1, wherein the liquid oil component comprises light mineral oil.

10. The method of claim 1, wherein the liquid oil component further comprises an emulsifying agent.

11. The method of claim 1, wherein the aqueous component further comprises one or more humectants, preservatives, chelating agents, emulsifying agents, thickening agents, or a combination thereof.

12. The method of claim 1, wherein the pharmaceutical composition further comprises a pH adjusting agent.

13. The method of claim 1, wherein the composition is formulated as a lotion.

14. The method of claim 1, wherein the dermatological or mucosal disorder or condition is psoriasis, plaque psoriasis, atopic dermatitis, contact dermatitis, hand dermatitis, eczema, seborrheic dermatitis, rash, or poison ivy dermatitis.

15. The method of claim 14, wherein the dermatological or mucosal disorder or condition is plaque psoriasis.

16. The method of claim 1, wherein the method comprises administering the pharmaceutical composition to the skin once daily or twice daily.

17. The method of claim 1, wherein the method comprises administering the pharmaceutical composition for a period of treatment longer than two weeks.

18. A method of treating a dermatological or mucosal disorder or condition, the method comprising topically administering a pharmaceutical composition comprising halobetasol propionate to the skin of an individual having the dermatological or mucosal disorder or condition, wherein the pharmaceutical composition comprises:

a liquid oil component comprising one or more monocarboxylic acid esters and/or dicarboxylic acid esters, and mineral oil, light mineral oil, or a combination thereof;

halobetasol propionate at a concentration of 0.01%, and wherein at least 25% of the corticosteroid is solubilized in the liquid oil component at a temperature of 22° C.+/−2° C.; and an aqueous component comprising water;

wherein the pharmaceutical composition is free of white petrolatum; and wherein the pharmaceutical composition is formulated as a lotion or a cream.

* * * * *